United States Patent [19]
Terwilliger

[11] Patent Number: 6,083,176
[45] Date of Patent: Jul. 4, 2000

[54] AUTOMATED BIOPSY NEEDLE HANDLE

[75] Inventor: Richard A. Terwilliger, Estes Park, Colo.

[73] Assignee: Medical Device Technologies, Inc., Gainesville, Fla.

[21] Appl. No.: 09/132,941

[22] Filed: Aug. 11, 1998

[51] Int. Cl.[7] ...................................................... A61B 10/00
[52] U.S. Cl. ........................................... 600/562; 600/567
[58] Field of Search ................................... 600/562, 564, 600/565, 566, 567, 568

[56] References Cited

U.S. PATENT DOCUMENTS

| | | |
|---|---|---|
| Re. 34,056 | 9/1992 | Lindgren et al. . |
| 3,090,384 | 5/1963 | Baldwin et al. . |
| 3,732,858 | 5/1973 | Banko . |
| 3,788,320 | 1/1974 | Dye . |
| 3,844,272 | 10/1974 | Banko . |
| 4,210,146 | 7/1980 | Banko . |
| 4,266,555 | 5/1981 | Jamshidi . |
| 4,403,617 | 9/1983 | Tretinyak . |
| 4,476,864 | 10/1984 | Tezel . |
| 4,570,632 | 2/1986 | Woods . |
| 4,600,014 | 7/1986 | Beraha . |
| 4,640,296 | 2/1987 | Schnepp-Pesch et al. . |
| 4,651,752 | 3/1987 | Fuerst . |
| 4,655,226 | 4/1987 | Lee . |
| 4,699,154 | 10/1987 | Lindgren . |
| 4,733,671 | 3/1988 | Mehl . |
| 4,747,414 | 5/1988 | Brossel . |
| 4,776,346 | 10/1988 | Beraha et al. . |
| 4,817,631 | 4/1989 | Schnepp-Pesch et al. . |
| 4,924,878 | 5/1990 | Nottke . |
| 4,958,625 | 9/1990 | Bates et al. . |
| 5,025,797 | 6/1991 | Baran . |
| 5,064,411 | 11/1991 | Gordon, III . |
| 5,220,926 | 6/1993 | Jones . |
| 5,316,013 | 5/1994 | Striebel, II et al. . |

FOREIGN PATENT DOCUMENTS

| | | |
|---|---|---|
| 0010321 | 4/1980 | Germany . |
| 0141108 | 4/1980 | Germany . |
| 175611 | 9/1965 | Russian Federation . |
| 709714 | 6/1954 | United Kingdom . |
| 748451 | 5/1956 | United Kingdom . |
| WO 83/03343 | 10/1983 | WIPO . |

*Primary Examiner*—Max Hindenburg
*Assistant Examiner*—Brian Szmal
*Attorney, Agent, or Firm*—Fliesler, Dubb, Meyer & Lovejoy LLP

[57] ABSTRACT

A novel automated handle assembly has an opening that allows for insertion of a needle set. The needle set is an integral unit and consists of an outer hollow cannula and an inner pointed tip stylet. The stylet and the cannula are capable of being urged forward separately into the biopsy area in a defined motion in relation to each other. The handle assembly includes a housing, a cannula extension and a stylet extension. In operation, the stylet and the cannula are inserted into the housing. The extensions are slidable and moved rearward separately until the stylet and the cannula are in a spring loaded position wherein first locking members have engaged second locking members on both the stylet and the cannula. The stylet and the cannula are inserted into a patient near the biopsy area. The stylet is then urged into the biopsy area. The stylet extension is pushed forward by a user's thumb and the stylet is fired so that the tissue is pierced. The cannula extension is triggered by the firing of the stylet and automatically urged forward so that the tissue is severed and captured in the notch of the stylet. After disengaging the biopsy area, the stylet is pressed forward using the extension of the stylet so that the tissue sample is exposed and may be removed. The stylet and cannula are then pulled back into the starting position so that multiple samples may be taken.

35 Claims, 13 Drawing Sheets

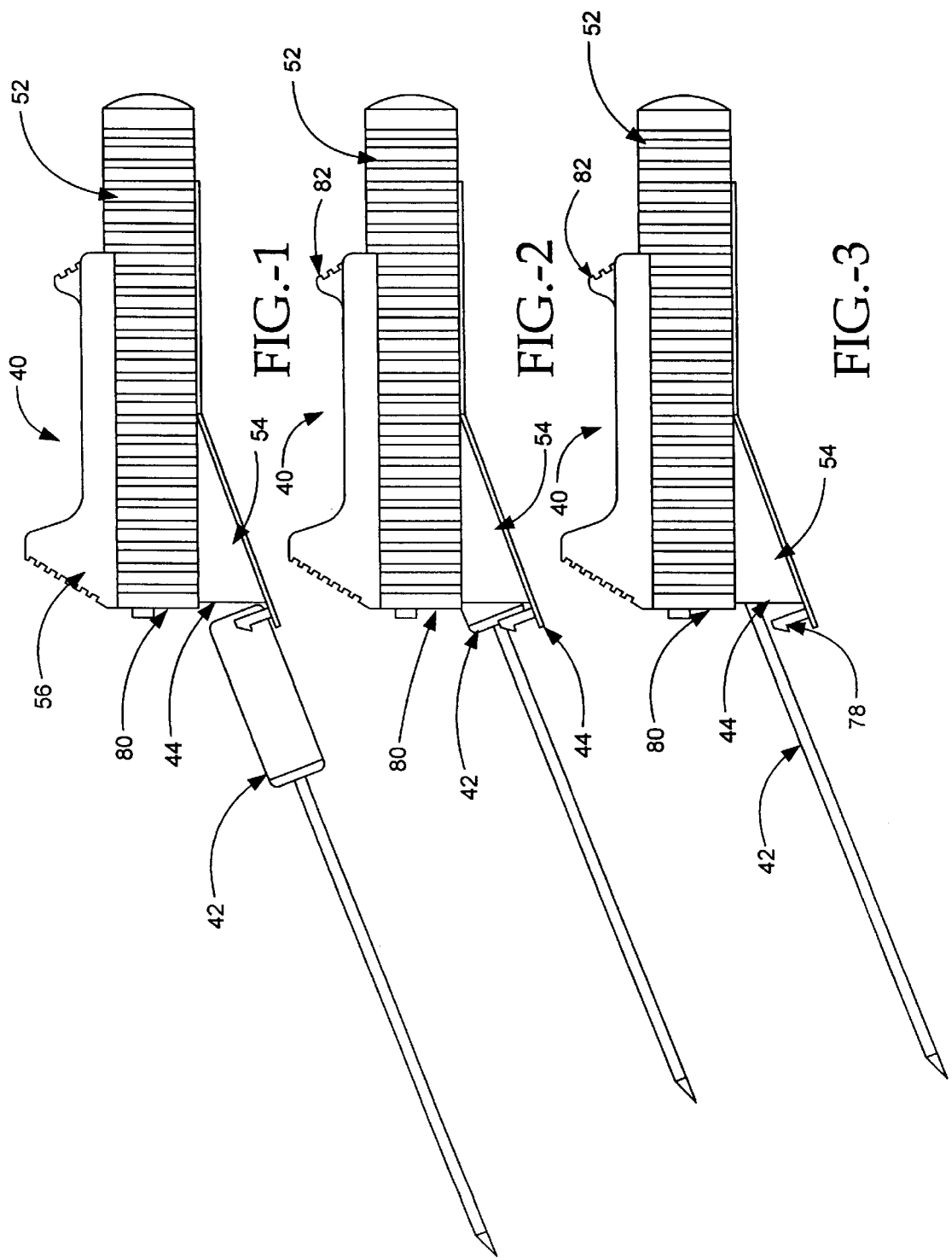

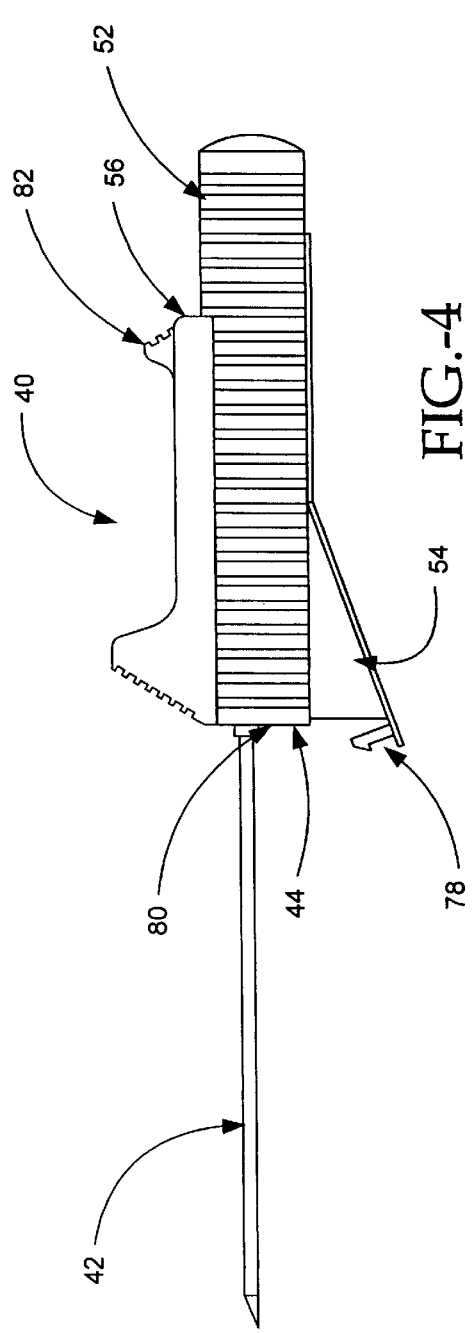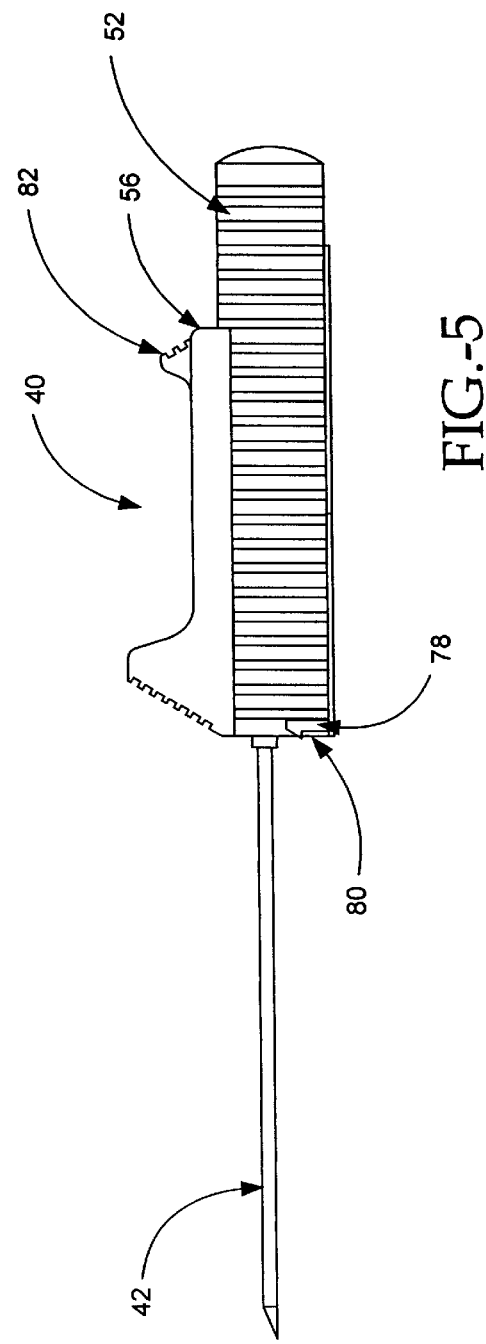

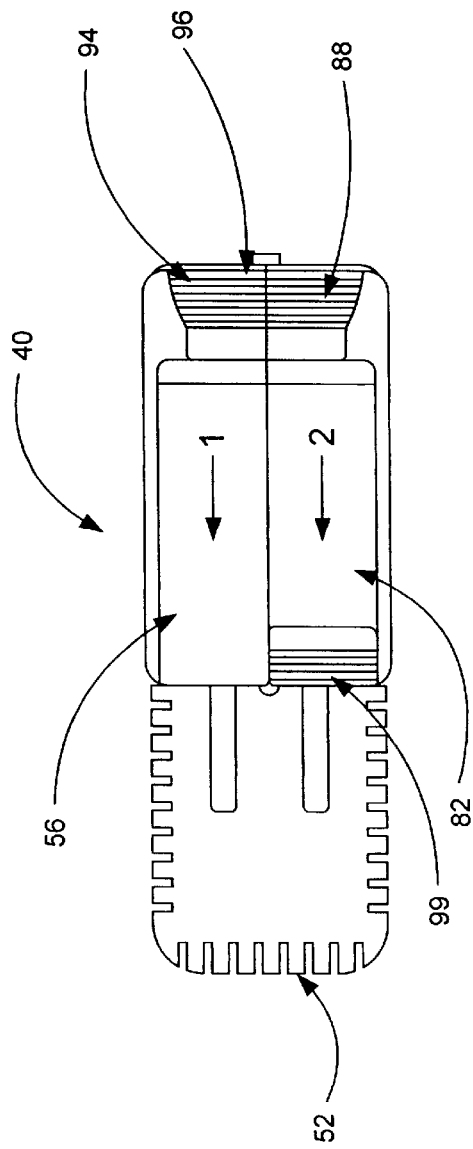
FIG.-8
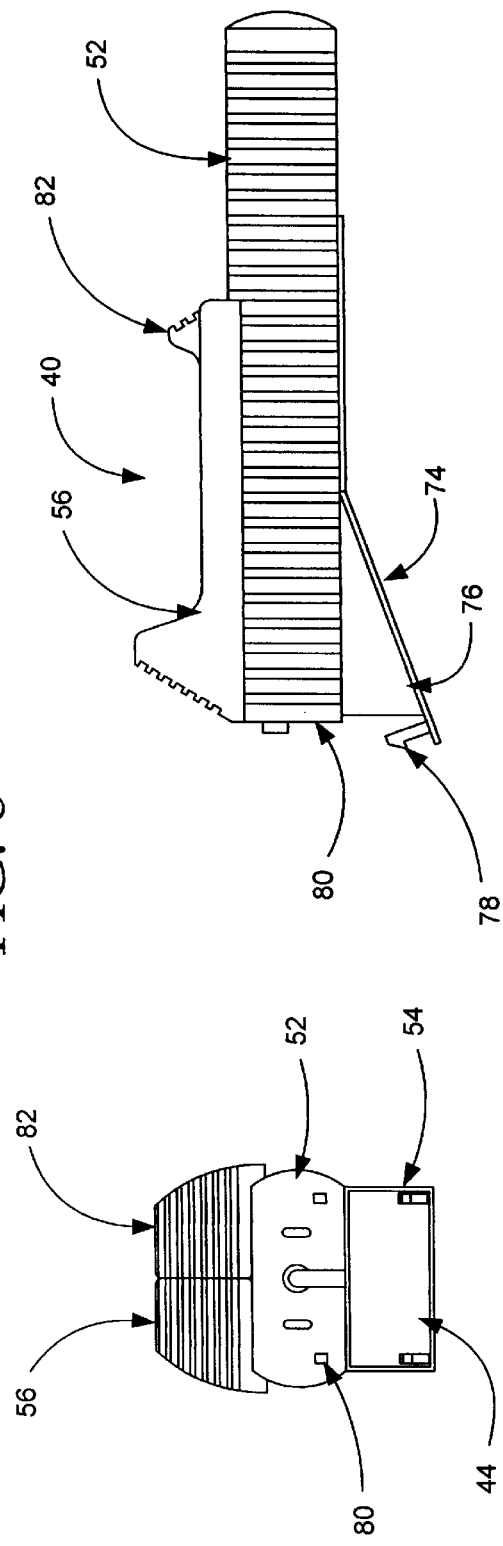
FIG.-9
FIG.10

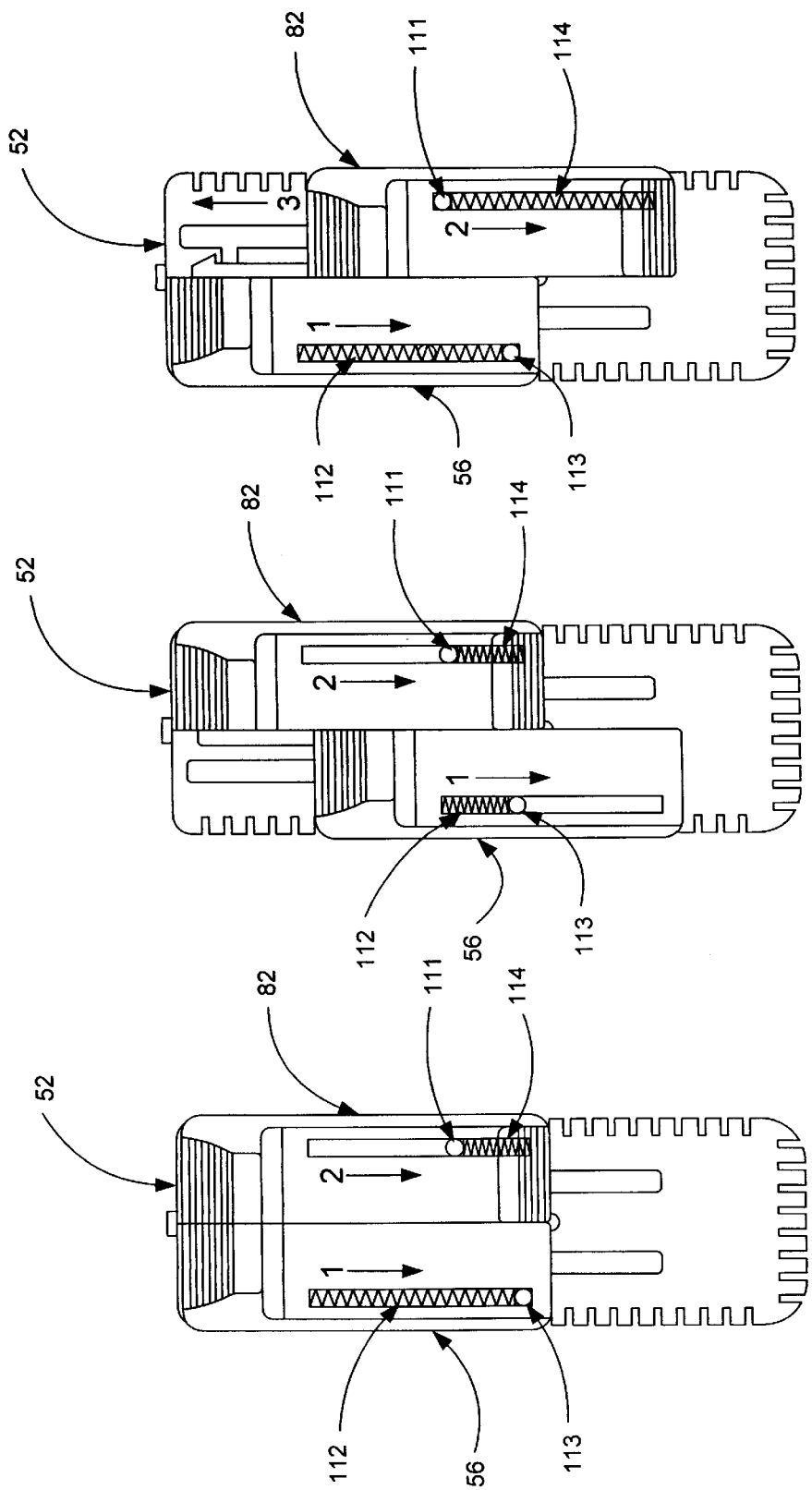

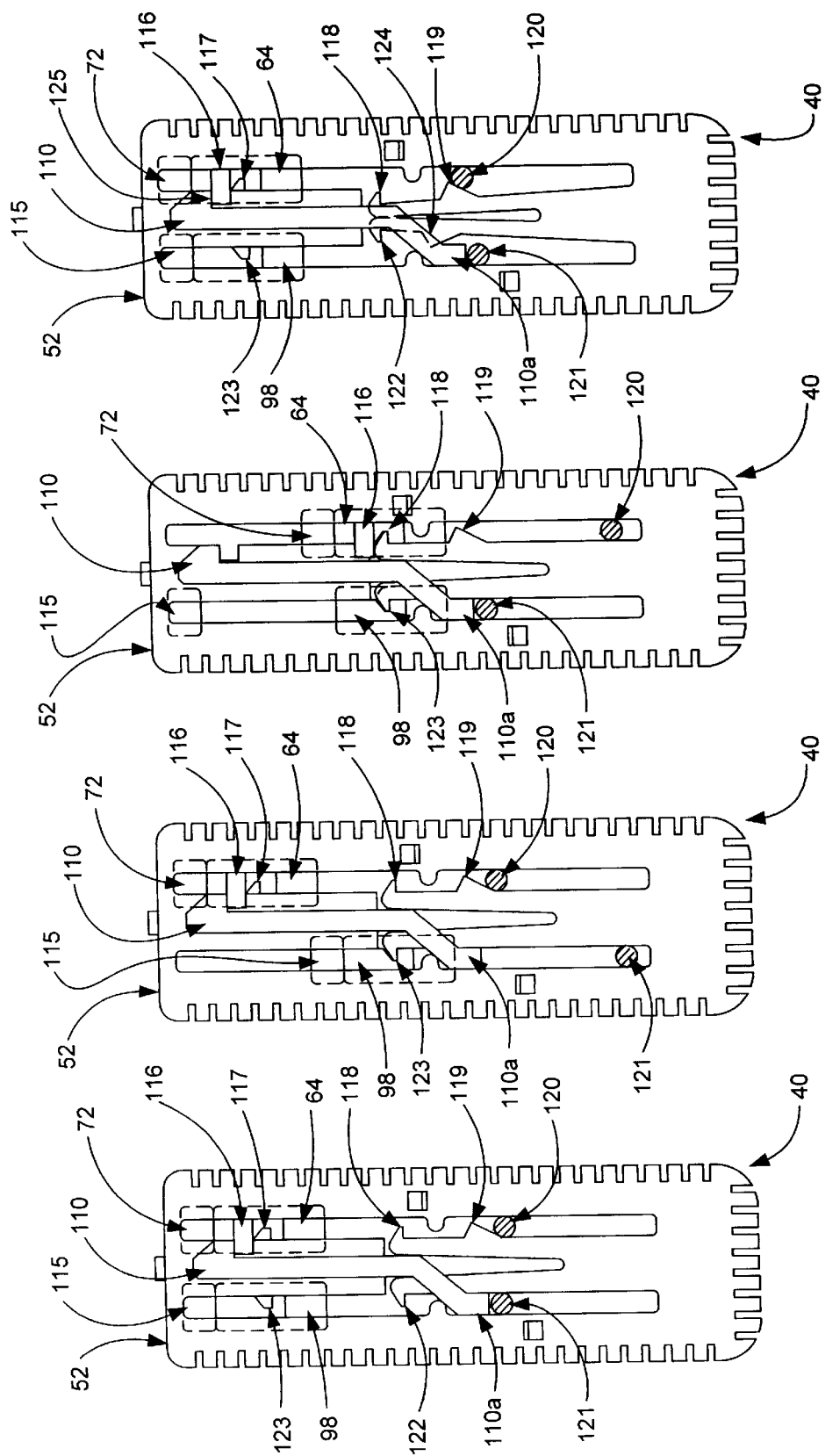

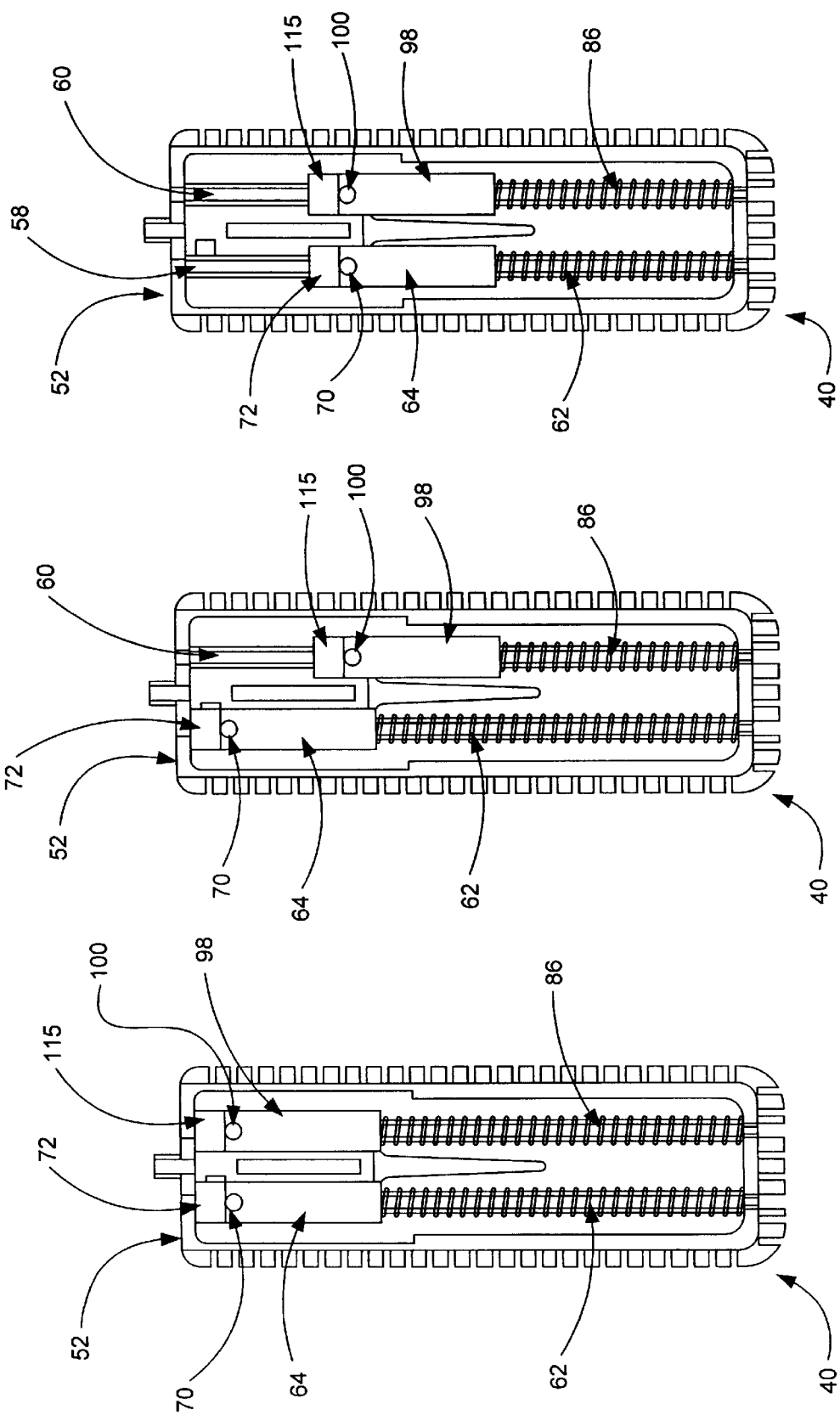

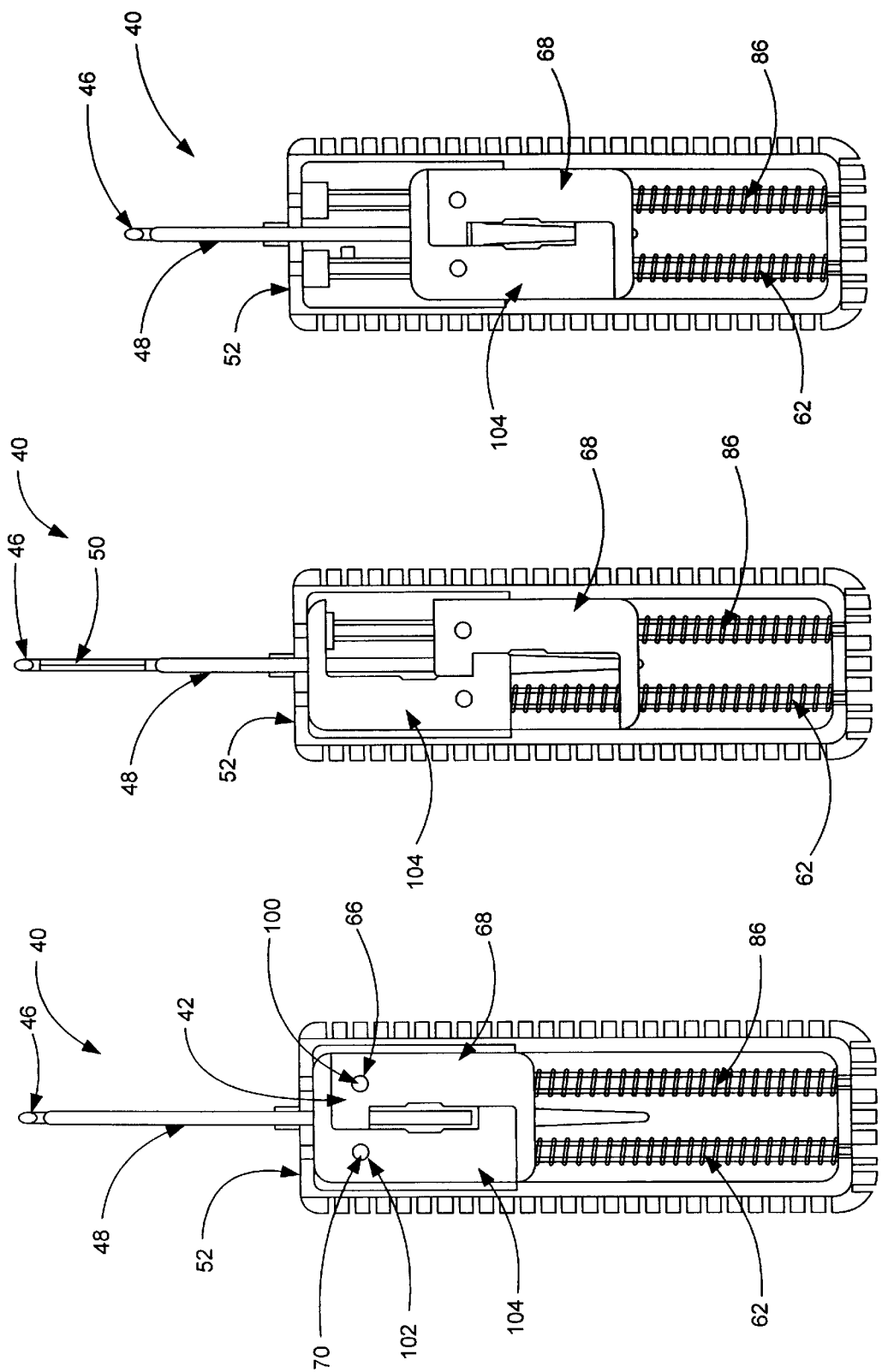

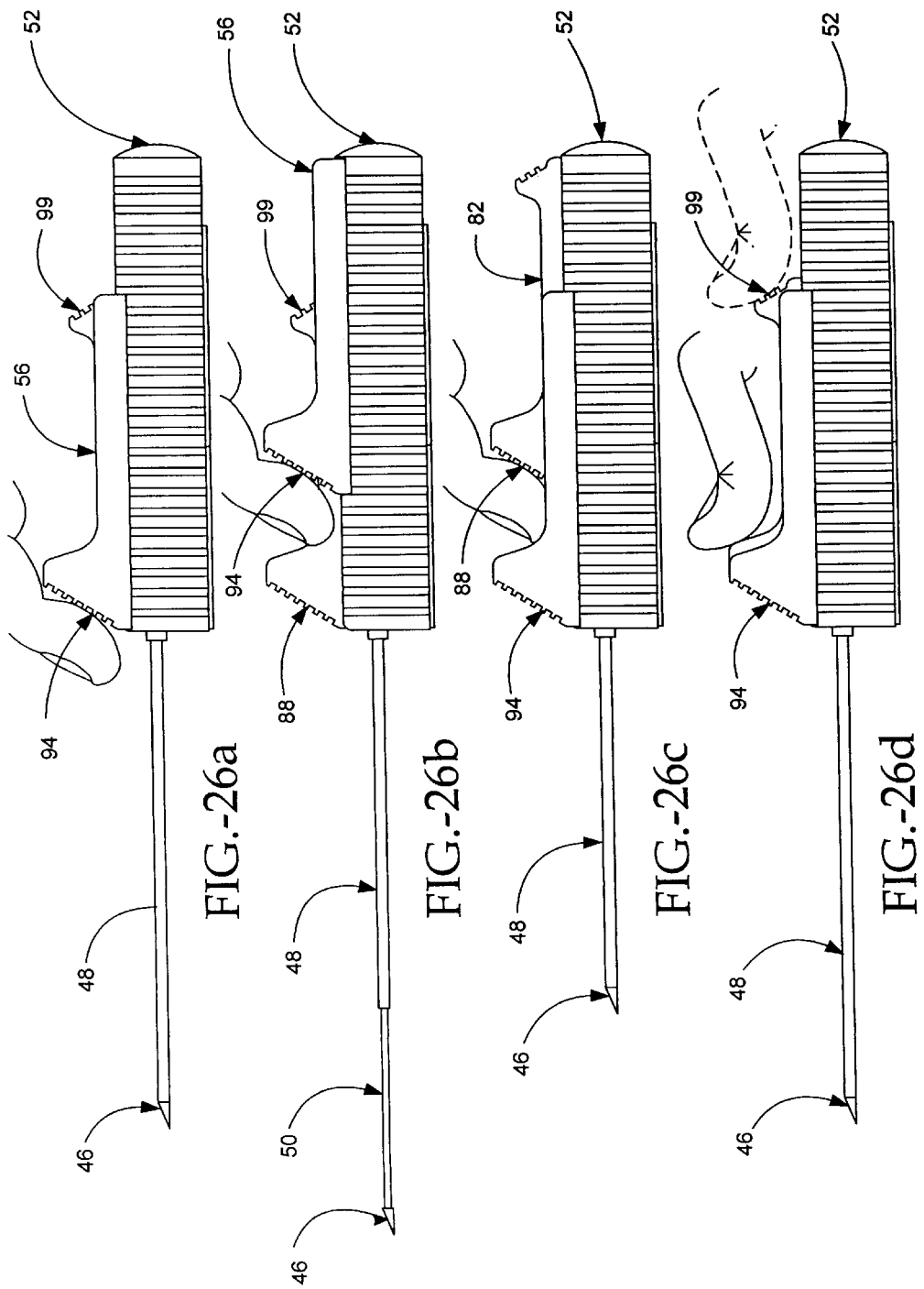

1

AUTOMATED BIOPSY NEEDLE HANDLE

CROSS REFERENCE TO RELATED APPLICATIONS

The present application is related to the following United States Patent Application, which application is by the same inventor as the present invention, and which application is incorporated by reference herein in its entirety:

U.S. patent application Ser. No. 09/076,181, entitled, "Biopsy Needle Handle", filed on May 12, 1998, and currently pending.

FIELD OF THE INVENTION

This invention relates to a new handle design which provides the means to hold, operate and actuate a needle set to collect a tissue sample from humans or animals by a procedure referred to as tissue biopsy, and more particularly to an improved handle device which can be used in automated biopsy procedures to assist in the extraction of tissue in a precise manner.

BACKGROUND OF THE INVENTION

It is often desirable and frequently absolutely necessary to sample or test a portion of tissue from humans and even animals to aid in the diagnosis and treatment of patients with cancerous tumors, pre-malignant conditions and other diseases or disorders. Typically in the case of cancer or the suspicion of malignant tumors, a very important process called tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration (hollow needle on a syringe) or a core biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed "blind" by the physician and guided by "feel" and known anatomic "landmarks".

Tumors are first noted in a patient by one of three ways, palpation, x-ray imaging or ultrasound imaging. Once a tumor is identified, a biopsy procedure is performed. Modern medical opinion dictates early detection of cancer, which increases the likelihood of successful treatment. Biopsy are performed on "Tumor Masses" as small as 2 millimeters in diameter. This procedure is performed under ultrasound or x-ray guidance. Tumors of this size cannot be biopsied reliably by hand since the tumor is about the same size as the biopsy needle. Manual attempts at biopsy can push the tumor away without piercing the mass. Automatic puncture devices are needed to accelerate the needle at such a velocity that even a small tumor can be pierced.

Two very important innovations in the field of medical technology have influenced the field of tissue biopsy in the last five years.

One, the use of tissue imaging devices which allow the physician to "see" inside the body and visually guide the needle to the tumor mass.

Two, the invention of the Automatic Core Biopsy Device (ACBD) or "Biopsy Gun". The ACBD is an instrument which propels a needle set with considerable force and speed to pierce the tumor mass and collect the tissue sample. This ACBD device has allowed physicians to test tissue masses in the early stages of growth and has contributed to the medical trend of early diagnosis and successful treatment of cancer.

Examples of such ACBD devices have been described with respect to the collection of tissue samples in U.S. Pat. Nos. 4,651,752, 4,702,260, and 4,243,048.

Historically, Automated Core Biopsy Devices (ACBD) have used the "Tru-Cut" needle set design. The "Tru-Cut" needle is comprised of an inner notched stylet with an outer cannula. The stylet is a needle with a notched cut out at the distal end. The cannula is a hollow needle with an angled cutting surface at the distal end which slides over the stylet. When the stylet is advanced into tissue under spring powered force, the tissue is pierced and relaxes into the notched cut out. When the cannula is slid forward, the tissue in the notch of the stylet is sliced off and retained in the notch until the cannula is drawn back. The "Tru-Cut" needle yields a core sample which is semi-circular in cross section, with length of the core sample determined by the stroke of the ACBD.

Subsequent improvements to the "Tru-Cut" needle design have been introduced and are described in U.S. Pat. No. 5,449,001.

There are numerous prior art devices on the market that employ this process. However, in prior art designs, if the physician requires a lightweight and simplistic biopsy device which utilizes single-handed automated deployment of the entire needle set for precision and simplicity, a problem is presented.

Furthermore, if the physician requires a biopsy device which cycles the needle set a short or longer distance into the tissue mass, a separate device for each needle distance desired has to be purchased. Current prior art devices have captive needle sets which require the physician to have many different styles of devices available to perform the range of procedures that are encountered in a biopsy procedure. This is a design limitation because it creates a situation of compromise between the physician's desire to use the optimum needle for a given procedure and the need to overstock all the possible combinations of needle gauges, lengths and predetermined extensions of the stylet that are available for a biopsy procedure. Furthermore, in the era of managed health care, the cost of biopsy procedures has come under scrutiny. The disposable single use devices are expensive and not desirable due to their high single use cost. Thus, prior art designs of the ACBD have a need for a design that allows the interchangeability of the needle sets to accommodate the parameters of the biopsy procedure to be performed.

On the other hand, the physician may use a prior art device that is capable of functioning automatically or at different distance settings to perform a range of biopsy procedures. However, such an automatic adjustable device is mechanically complicated and requires external settings to be made to allow the mechanism to perform. Also the reusable handles have, in prior art, been costly to obtain because of the expense of manufacturing a complicated mechanical design. Since the mechanism of the prior art ACBD is designed to have a stylet that moves forward first and then activates the cannula, thus advancing the needles in their proper sequence, these prior art devices require many high tolerance mechanical moving parts with precision bushings in order to have the device operate properly. The required repeated use of the reusable design dictates that the mechanical design be robust and operate many cycles without undue wear or failure. These requirements have produced in prior art, ACBDs that are heavy, large and costly due to their complicated mechanical designs.

Thus, the size, weight and expense of single use and reusable prior art ACBD's have limited their use. An improved design is needed that gives the physician an automatic, small, light weight, easy to single-handedly operate and cost effective design that improves the function of obtaining a tissue sample.

SUMMARY OF THE INVENTION

It is therefore an advantage of the present invention to provide a handle assembly for a needle set which automatically captures and allows the removal of a tissue sample from a tissue mass for examination in one operation.

It is another advantage of the present invention to provide a handle assembly which can reliably obtain biopsy samples, is simple in design, easy to use and cost effective.

It is a further advantage of the present invention to provide a handle assembly for a needle set with a mechanism to single handedly operate the cocking of each stage and the subsequent firing of both stages with out repositioning the hand.

It is another advantage of the present invention to provide a handle assembly which allows the user to obtain a tissue sample of a predetermined size.

It is yet another advantage of the present invention to provide a handle assembly which allows the user to choose the parameters of the needle set to be used to obtain the optimal tissue samples for any given biopsy procedure.

It is a further advantage of this invention to provide a handle assembly for a needle set with spring powered stages to actuate the stylet and cannula to assist in severing the tissue from the surrounding biopsy site.

It is another advantage of the present invention to provide a handle assembly for a needle set which incorporates a safety feature therein to prevent accidental firing.

It is yet a further advantage of this invention to provide a handle assembly for a needle set which allows the single handed operation of locking the spring powered stages for the cannula and stylet.

It is another advantage of the present invention to provide a handle assembly for a needle set which provides the firing mechanism in the same component that cocks the spring loaded coupling.

It is yet a further advantage of this invention to provide a handle assembly for a needle set which incorporates the cocking of the cannula and stylet, the safety feature and the firing mechanism in a single assembly, thus allowing real single-handed operation without the need of separate components, buttons or slides to activate each of these actions.

It is a further advantage of this invention to provide a handle assembly for a needle set that is disposable and can be delivered sterilized prior to the procedure.

It is another object of this invention to provide a handle assembly for a needle set which can be used to obtain multiple tissue samples from the same biopsy site.

These and other advantages of the invention will be apparent from the following descriptions and claims.

In accordance with the present invention and new and improved automated biopsy handle assembly for a needle set is provided. The handle assembly has an opening that allows for the insertion of a needle set. The needle set consists of an outer hollow cannula and an inner pointed tip stylet.

The handle assembly includes a housing, a locking lid, a cannula extension and a stylet extension. The housing is rectangular in shape and has a hollow inside. The cannula extension and the stylet extension are slidably attached to the top of the housing, and the locking lid extends from the bottom of the housing, with the inner mechanisms shielded therebetween. Inside the housing are two cylindrical rods which guide the stylet and cannula when a biopsy is performed and a tissue sample retrieved. The rod which guides the cannula has mounted thereon a spring and a cannula coupling for securing the cannula in the housing. The cannula includes an aperture in its base for connecting to a protrusion on the cannula coupling. The cannula coupling is pushed against the spring by a cannula pushing member, which is attached to the cannula extension, until it reaches a position wherein the cannula is spring loaded and ready for release.

Similarly, the rod which guides the stylet has mounted thereon a spring and a stylet coupling for securing the stylet in the housing. The stylet includes an aperture in its base for connecting to a protrusion on the stylet coupling. The stylet coupling is pushed against the spring by a stylet pushing member, which is attached to the stylet extension, until it reaches a position wherein the stylet is spring loaded and ready for release. Once the stylet is released, the spring urges the stylet forward in a rapid motion piercing the tissue. The cannula is then automatically released wherein the spring urges the cannula forward in a rapid motion severing the prolapsed tissue which resides in the notch of the stylet.

The locking lid covers the bottom of the housing and has a descending portion having side walls which provides the opening for insertion of the needle set. The front of the locking lid includes a catch on each side which engages a cut-out located on the front side of the housing. Once the needle set is inserted, the descending portion is pushed up to be flush with the bottom of the housing and the needle set is secured inside the housing by engagement of the catch and cut-out on each side of the front of the housing. The locking lid ensures one patient use of the biopsy needle set and housing.

The cannula extension and the stylet extension cover the top of the housing. Alternatively, the extensions may be called actuators. The extensions advantageously adapt the handle to one-hand operation by the user. The stylet extension also includes a protrusion. The stylet extension, together with the protrusion are pushed forward, until the protrusion interacts with a locking member protrusion to release the stylet. The stylet coupling then moves forward releasing the cannula side of the mechanism which will be explained later.

At the front of each slidable extension, a pushing portion is provided. The pushing portions include ribs for enhanced friction between the user's thumb and the pushing portion during the biopsy procedure. The stylet extension also includes a pushing portion on the back end for actuating the stylet. Located inside, behind the stylet extension near the front of the housing is a stylet coupling for engaging the stylet in the housing. The stylet coupling includes a protrusion which is inserted into an aperture located on the base of the stylet. Similarly, located inside, behind the cannula extension near the front of the housing is a cannula coupling for engaging the cannula in the housing. The cannula coupling includes a protrusion which is inserted into an aperture located on the base of the cannula.

In operation, the needle set, including the stylet and cannula, are inserted into the handle assembly in the descending portion of the locking lid, which is then pushed upward and secured via the catch and the cut-out located on the front of the locking lid and the housing, respectively. The cannula extension is moved rearward, with a single user's hand, until the cannula is in the spring loaded position and the first locking member has engaged the second locking member. A return spring under the cannula extension returns it to its original position after the first locking member is engaged. The stylet extension is then moved rearward, with a single user's hand, until the stylet is in the spring loaded position and the first locking member has engaged the second locking member. A bias spring under the extension maintains the extension in the rearward position after the second locking member is engaged. With the same single user's hand, the stylet and the cannula are inserted into the patient near the biopsy area. The stylet is then urged forward against the bias spring by pushing the stylet extension forward with the user's thumb. This bias spring keeps the stylet extension in the rearward position and prevents accidental firing until the operator pushes the stylet extension forward. The stylet is released and fired forward thereby automatically releasing the cannula. The tissue is severed and captured in the notch of the stylet. After removing the needle set from the biopsy site, the cannula is pressed back using the cannula extension so that the tissue sample is exposed and may be removed. The stylet is then pulled back into the starting position. Moving the stylet extension rearward again reestablishes the stylet and the cannula in relation to each other in order to allow subsequent reinsertions into the biopsy area for additional tissue samples. Accordingly, the inventive biopsy handle allows the user the ability to take multiple tissue samples conveniently and quickly using only a single hand.

BRIEF DESCRIPTION OF THE FIGURES

The above and other advantages of the present invention will be apparent upon consideration of the following detailed description, taken in conjunction with the accompanying drawings, in which like reference characters refer to like parts throughout, and in which:

FIGS. 1–5 are side views of an embodiment of the handle assembly of the present invention showing insertion and securing of the needle set into the locking lid and housing according to the present invention;

FIG. 8 is a top view of an embodiment illustrating a cannula and a stylet slidable extension attached to a housing according to the present invention;

FIG. 9 is a side view of an embodiment of the handle assembly showing the housing, the cannula and the stylet slidable extensions and a locking lid according to the present invention;

FIG. 10 is a front view of an embodiment of the handle assembly showing the locking lid extended in an open position according to the present invention;

FIG. 12 is a top view of an embodiment of a housing assembly showing the two extensions and the return springs under the extensions according to the present invention;

FIG. 13 is a top view of an embodiment of the housing assembly showing the cocking of the cannula extension according to the present invention;

FIG. 14 is a top view of an embodiment of the housing assembly showing the cocking of the stylet extension according to the present invention;

FIGS. 15–18 are top views showing an embodiment of the inner mechanisms of the slidable extensions and the housing at various stages of cocking and releasing the cannula and stylet couplings according to the present invention;

FIGS. 19–21 are inside bottom views of an embodiment of the housing at various stages of cocking the cannula and stylet couplings sequentially according to the present invention;

FIGS. 22–24 are inside bottom views of an embodiment of the housing having a needle set at various stages of sequentially cocking the attached needle set according to the present invention;

FIGS. 25a–e and 26a–d are side views of an embodiment of the handle assembly having a needle set illustrating the sequencing of the extensions and the sequence of needle set action in retrieving a tissue sample according to the present invention;

DETAILED DESCRIPTION OF THE PREFERRED EMBODIMENT

Figure 7:
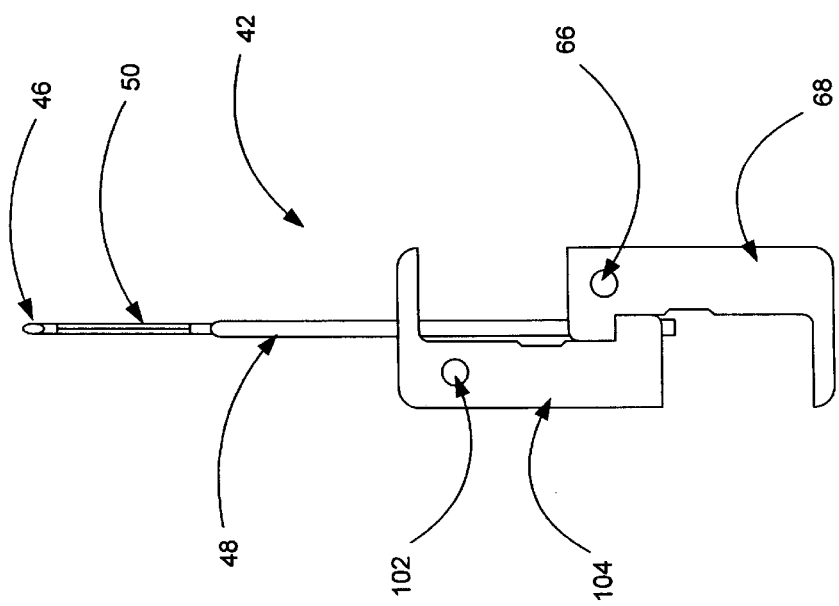
FIGS. 6–7 are top views of a needle set.
Figure 6:
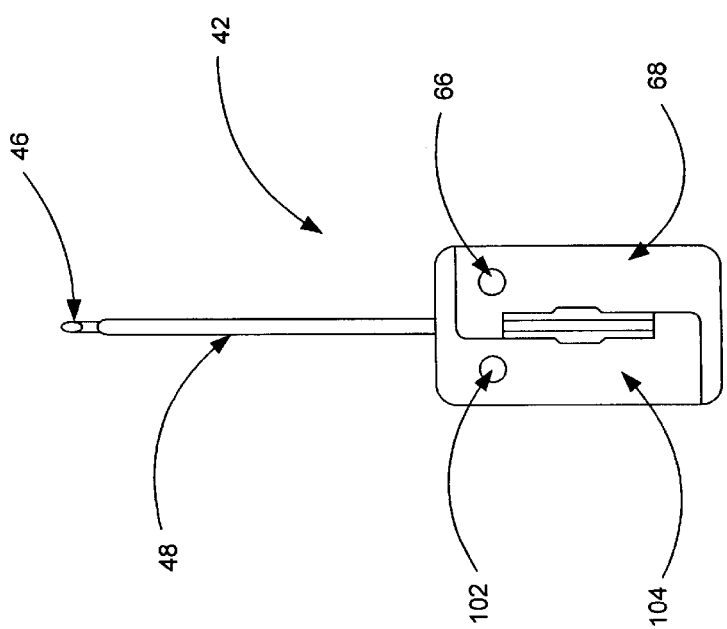

The present invention will now be described with reference to FIGS. 1 through 31 which in general relate to a novel handle assembly which can be used in an automated biopsy procedure to assist in the extraction of tissue in a precise manner using only one of a user's hands. It is understood that the principles of the present invention may be suitable for a variety of functions and incorporated into various biopsy devices Referring now to FIGS. 1 through 7, there is shown a handle assembly 40 and a needle set 42. The handle assembly 40 has an opening 44 that allows for the insertion of the needle set 42 as will be explained hereinafter. The needle set 42 (which is not part of this invention) is an integral unit and consists of an inner pointed tip stylet 46 and an outer hollow cannula 48, as shown in FIGS. 6 and 7. The stylet 46 and the cannula 48 are capable of being urged forward separately into the biopsy area in a defined motion in relation to each other. The stylet 46 includes a notch 50 which is ground at the distal end of the needle and is a repository for the tissue that is pierced by a forward motion of the needle. The secondary motion of the cannula 48 coaxially over the stylet 46 cuts and captures the tissue in the notch 50 of the needle, thus allowing the tissue to be removed from the biopsy area and examined outside the patient.

With reference to FIGS. 8 through 11, the handle assembly 40 will now be described. The handle assembly 40 includes a housing 52, a locking lid 54, a cannula extension 56 and a stylet extension 82. The housing 52 is rectangular in shape and has a hollow inside. The cannula extension 56 and the stylet extension 82 are slidably attached to the top of the housing 52 by protrusions 120 and 121, respectively, and are single hand-operated extensions. Alternatively, the extensions may also be called actuators. The locking lid 54 is attached to the bottom of the housing 52. The extensions and the locking lid shield the inner mechanisms of the handle assembly, as will be explained hereinafter. The preferred material for the handle assembly 40 is a lightweight plastic although it is understood that the handle assembly may be formed with metals, polymers and other materials. Moreover, the handle assembly may be disposable and delivered sterilized prior to the biopsy procedure or not.

Inside the housing 52 are two cylindrical rods 58, 60 (FIG. 21) which guide the stylet and cannula when a biopsy is performed and a tissue sample retrieved. The rod 60, which guides the cannula 48, includes a spring 86 and a cannula coupling 98 for engaging the cannula in the housing. The cannula 48 (FIG. 6) includes an aperture 66 in its base 68 for connecting to a protrusion or pin 100 (FIG. 19) on the cannula coupling 98. The cannula coupling 98 is pushed against the spring 86 by a cannula pushing member 115, which is attached to the cannula extension 56 (FIG. 8), until it reaches a position wherein the cannula 48 is spring loaded (i.e. in a spring compressed state) and ready for release. The spring loaded position is obtained when a second locking member 123 (FIGS. 15–18) on the cannula coupling 98 engages a first locking member 122 as explained hereinafter. Once the spring loaded position is obtained, a return spring 112 moves the cannula extension 56 back to its forward position (FIGS. 12–14). A spring stop 113 is included for providing a biasing force against the spring stop 113 when the cannula extension 56 is moved rearward.

The rod 58, which guides the stylet, includes a spring 62 and a stylet coupling 64 for engaging the stylet in the housing (FIGS. 19–21). The stylet coupling 64 also includes an actuating pin 116 (FIGS. 15–18) for striking a front projection on an actuating arm 110 thereby automatically releasing the cannula after the stylet has been fired. The stylet 48 (FIG. 6) includes an aperture 102 in its base 104 for connecting to a protrusion or pin 70 (FIG. 19) on the stylet coupling 64. The stylet coupling 64 is pushed against the spring 62 by a stylet pushing member 72, which is attached to the stylet extension 82 (FIG. 21), until it reaches a position wherein the stylet 48 is spring loaded (i.e. in a spring compressed state) and ready for release. The spring loaded position is obtained when a second locking member 117 (FIGS. 15–18) on the stylet coupling 64 engages a first locking member 118 as explained hereinafter. Once the stylet 48 is the spring loaded position, a bias spring 114 maintains the stylet extension 82 in the rearward position until the operator pushes it forward to release the stylet (FIGS. 12–14). A spring stop 111 is also included for providing a force against the bias spring 114 when the spring and the stylet extension is in its forward position. It is understood that no safety mechanism is necessary in the present invention as the locking of the stylet extension serves as a safety feature since a large amount of manual forward force and motion is required to overcome the force of spring 62 when firing the stylet. In FIGS. 15–18, once extension 82 is urged forward releasing second locking member 117 from first locking member 118 (a trip protrusion 120, which is attached to extension 82, deflects a stylet locking member protrusion 119), the actuating pin 116 of stylet coupling 64 strikes the front projection 125 (FIG. 18) of actuating arm 110 and pulls it slightly forward. This results in a back projection 110a of actuating arm 110 being urged against and deflecting a cannula locking member protrusion 124 thereby releasing the first locking member 122 of the cannula coupling 98 from the second locking member 123. Once the cannula 48 is released, the spring 86 urges the cannula 48 forward in a rapid motion severing the prolapsed tissue which resides in the needle notch.

Figure 11:
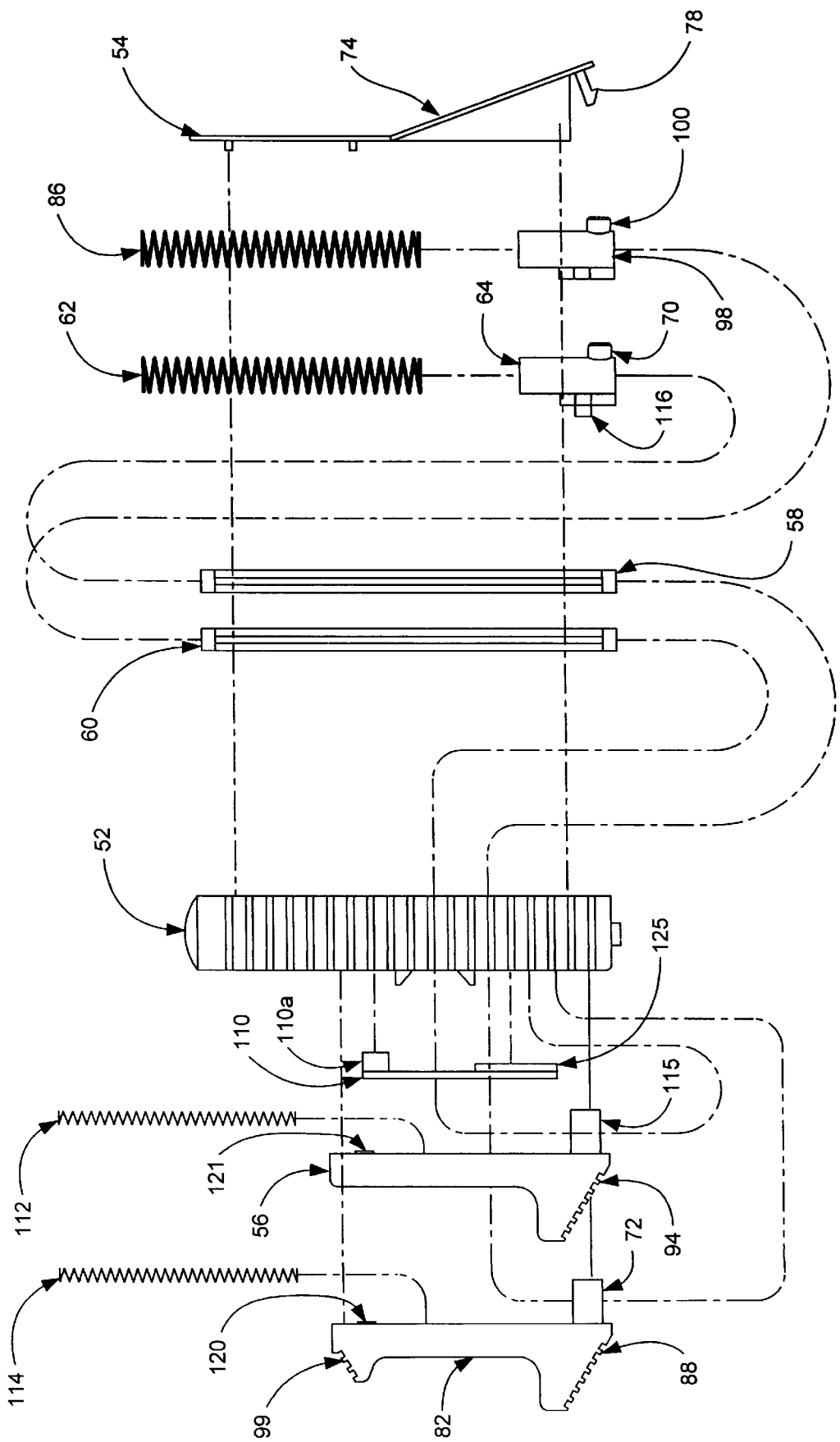
FIG. 11 is an exploded side view of an embodiment of the handle assembly according to the present invention.
Figure 25A:
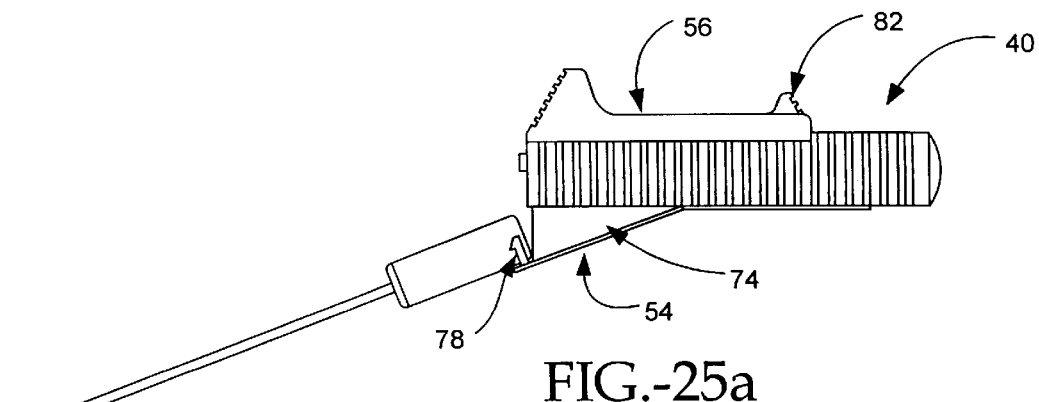
Figure 25B:
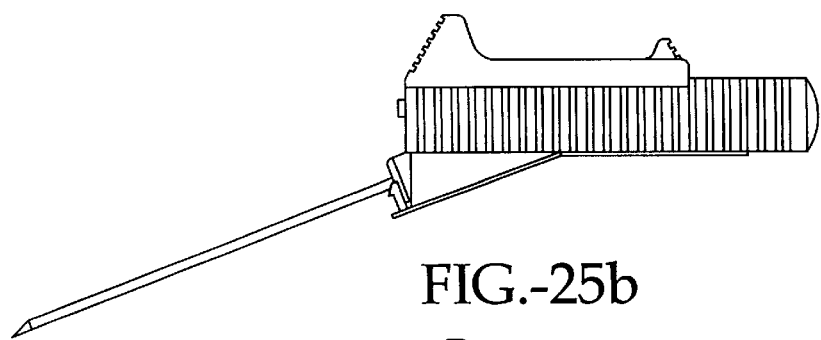
Figure 25C:
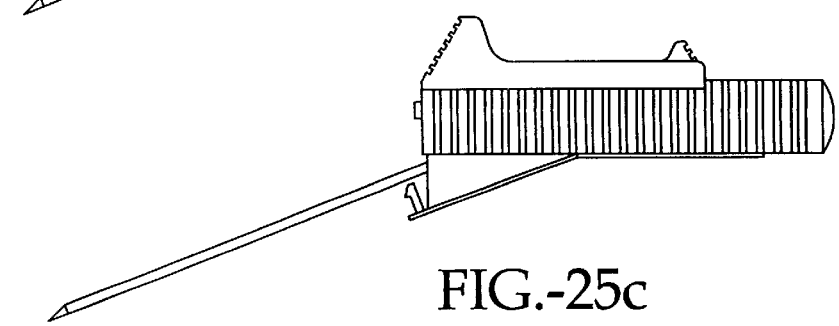
Figure 25D:
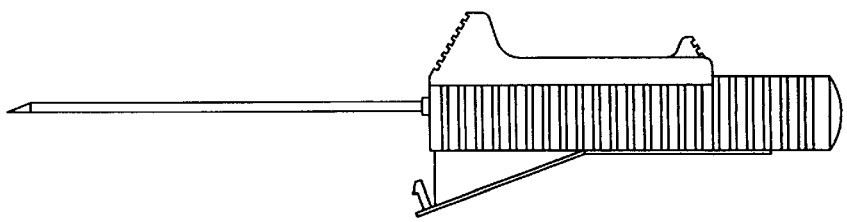
Figure 25E:
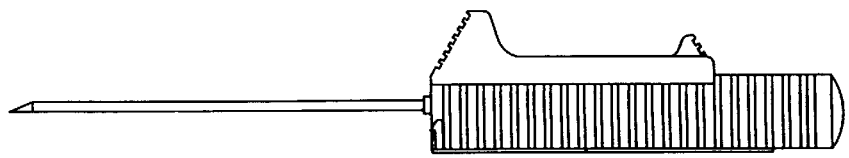
Figures 27, 28, 29:
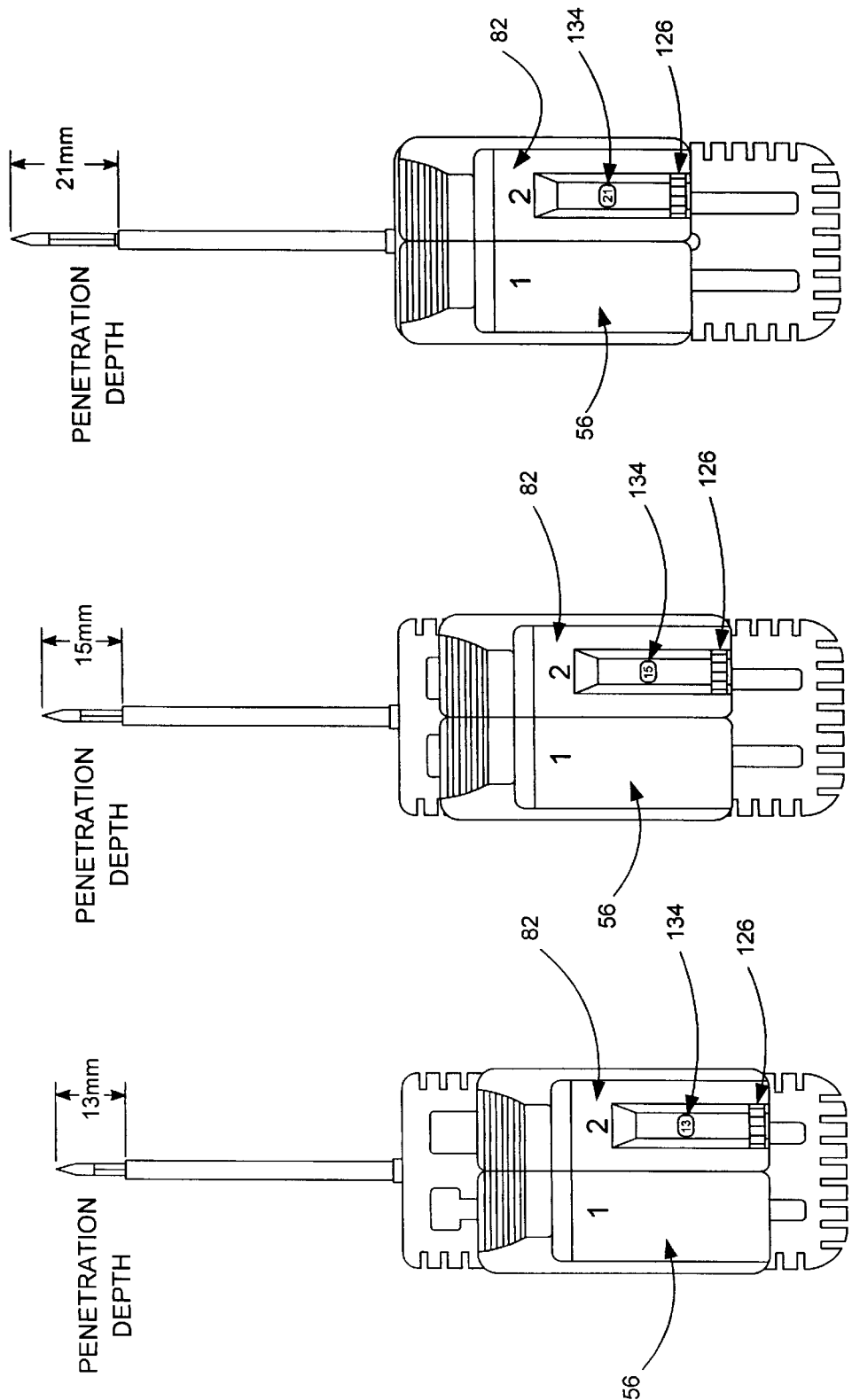
FIGS. 27–29 are top views showing of an embodiment of a housing assembly showing the extension having an adjustable wheel wherein the stylet needle is extended to various predetermined lengths.
Figure 30:
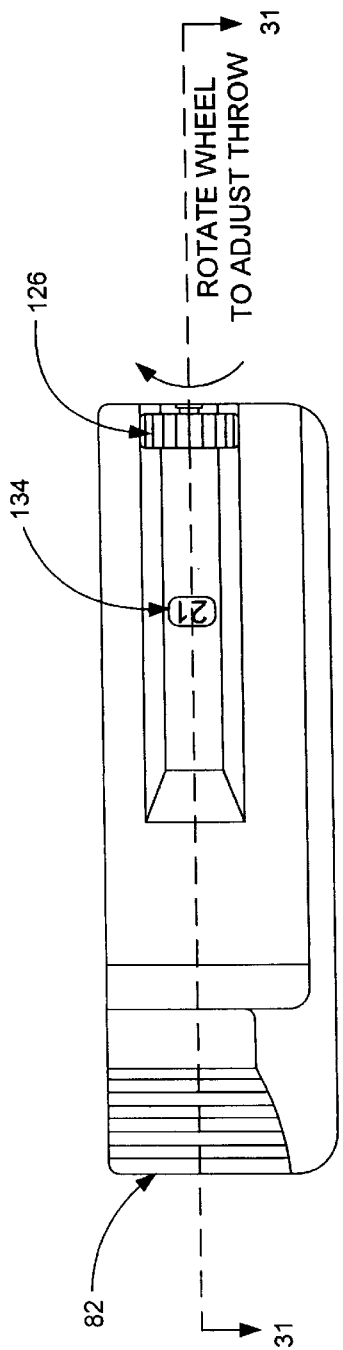
FIG. 30 is a top view of an embodiment of the slidable extension of the handle assembly illustrating the numeric indicator and the window according to the present invention.

Referring now to FIGS. 9 through 11, the locking lid 54 is shown. The locking lid 54 covers the bottom of the housing 52 and has a descending portion 74 having side walls 76 which provides the opening 44 for insertion of the needle set. The front of the locking lid includes a catch 78 on each side which engage a cut-out 80 (FIG. 1) located on the front of the housing 52. Once the needle set is inserted, the descending portion 74 is pushed up so that it is flush with the bottom of the housing 52 and the needle set is secured inside the housing by engagement of the catches 78 in cut-outs 80 on the front of the housing. The catches 78 are hook-shaped so as to allow the catches 78 to be easily urged into the cut-outs 80. Once in place, the front edge of the hook-shaped catches 78 snaps into locking the catches in the cut-outs.

At the front of the cannula extension 56, a pushing portion 94 (FIG. 8) is provided. The pushing portion 94 includes ribs 96 for enhanced friction between the user's thumb and the pushing portion during the biopsy procedure when the cannula extension is moved rearward. On top of the cannula extension 56, a number one (1) is indicated showing the sequence of actions required to take a tissue biopsy (FIGS. 12–14). The extension 56 is moved rearward in a first step. Located behind and axially of the slidable extension 56 near the front of the housing is the cannula coupling 98 for securing the cannula 48 and the cannula pushing member 115 (FIGS. 19–21) and for pushing the cannula coupling 98 against the spring 86. When the handle assembly is assembled, the cannula coupling 98 and the cannula pushing member 115 are located within the housing 52. The cannula coupling 98 includes a protrusion or pin 100 which is inserted into an aperture 66 (FIGS. 6–7) located on a base 68 of the cannula 48 as previously described heretofore.

Similar to the cannula extension 56, a pushing portion 88 (FIG. 8) is provided at the front of the stylet extension 82. The pushing portion 88 includes ribs 96 (FIG. 8) for enhanced friction between the user's thumb and the pushing portion when the stylet extension is moved rearward during the biopsy procedure. A second pushing portion 99 is also provided for single-handedly firing the stylet 46 forward, then sequentially the cannula 48, into the biopsy area. On top of the stylet extension 82, a number two (2) is indicated showing the sequence of actions required to take a tissue biopsy (FIGS. 12–14). The stylet extension 82 is moved rearward in a second step after the cannula extension 56 is moved rearward first. Located behind and axially of the stylet extension 82 near the front is a stylet coupling 64 for securing the stylet 46 and the stylet pushing member 72 (FIGS. 19–21) and for pushing the stylet coupling 64 against the spring 62. When the handle assembly is assembled, the stylet coupling 64 and the stylet pushing member 72 are located within the housing 52. The stylet coupling 64 includes a protrusion or pin 70 which is inserted into an aperture 102 (FIGS. 6–7) located on a base 104 of the stylet 46.

Considering FIGS. 15 through 18, in detail, these figures depict top cross-section views of the handle assembly 40 showing the operation of the internal parts and mechanisms associated with the cannula extension 56 and the stylet extension 82. FIG. 15 shows the mechanisms of the slidable extensions which move the stylet and the cannula. The stylet pushing member 72 and the cannula pushing member 115, which are attached to the stylet extension 82 and the cannula extension 56, are shown in a starting position, along with the stylet coupling 64 and the cannula coupling 98, respectively. FIG. 16 shows the cannula being forced rearward by the cannula extension 56 and the cannula pushing member 115 on the cannula extension 56 until the first locking member 122 engages the second locking member 123 on the cannula coupling member 98 and the cannula is cocked. FIG. 17 shows the stylet 46 being forced rearward by the stylet extension 82 and the stylet pushing member 72 on the stylet extension 82 until the first locking member 118 engages the second locking member 117 on the stylet coupling member 64 and the stylet 46 is cocked. FIG. 18 shows the trip protrusion 1 20 being moved forward by the stylet extension 82 until the stylet locking member protrusion 119 is deflected to the point of releasing the first locking member 118 from the second locking member 117 of the stylet coupling 64. The stylet of the needle set is then urged rapidly forward by the spring in order to pierce tissue. With regard to the firing of the cannula 48, the cannula 48 is actuated when the actuating pin 116 hits the front projection 125 of the actuating arm 110 pulling it forward, which then moves the back projection 110a of actuating arm 110 thereby deflecting the cannula locking member protrusion 124 to the point of releasing the first locking member 122 from the second locking member 123 of the cannula coupling 64. The cannula of the needle set is then urged rapidly forward by the spring in order to pierce tissue.

Considering FIGS. 19–21, in detail, these figures depict cross-section inside bottom views of the embodiment of the handle assembly 40. FIG. 19 shows the stylet coupling 98 and the cannula coupling 64 in the starting position. The protrusions or pins 70, 100 of stylet coupling 98 and the cannula coupling 64 are inserted into the apertures 66, 102 located on the bases of the stylet 46 and of the cannula 48, and thereby position the stylet 46 and cannula 48 relative to the housing 52 of the handle 40 (FIG. 22). The cannula extension 56 (FIG. 8) is connected to the cannula pushing member 115 and the stylet extension 82 is connected to the stylet pushing member 72. The rods 58, 60 are provided for guiding the stylet and the cannula in the housing 52 via the stylet coupling 64 and the cannula coupling 98, respectively. The spring 62 is also provided for powering the stylet when it severs the tissue captured in the notch of the stylet. Spring 86 provides power for the cannula. FIG. 20 shows the cannula coupling 98 being moved rearward at the point where the first locking member 122 engages the second locking member' 123 (FIG. 16). FIG. 21 shows the stylet coupling 98 being moved rearward at the point where the first locking member 118 engages the second locking member 117.

Considering FIGS. 22–24, in detail, these figures depict bottom cross-section views of the handle assembly 40 including the needle set 42 showing the operation of the cannula extension 56 (FIG. 8), the stylet extension 82 (FIG. 8) and the related internal parts that detail the stages of the biopsy procedure. FIG. 22 shows the needle set 42 and the handle assembly 40 in the starting position. The apertures 66, 102 on both the stylet and the cannula are engaged with the protrusions or pins 70, 100 on the stylet coupling and cannula coupling, respectively. FIG. 23 shows the cannula 48 after the cannula has been moved rearward and the first locking member 122 has engaged the second locking member 123 (FIG. 16). FIG. 24 shows the assembly wherein the stylet 46 has been urged backward and remains in the spring loaded position ready for release.

As shown in FIGS. 25a–e, the needle set 42 is inserted into the handle assembly 40 in the descending portion 74 of the locking lid 54 which is then pushed upward and secured via the catch 78 and the cut-outs 80 located on each side of the locking lid and the front of the housing, respectively. In a single-handed operation shown in FIGS. 26a–d, the cannula extension 56 is moved rearward until the cannula 48 is in the spring loaded position and the first locking member 122 has engaged the second locking member 123 (FIG. 26b). The stylet extension 82 is then moved rearward until the stylet 48 is in the spring loaded position and the first locking member 118 has engaged the second locking member 117 (FIG. 26c). The stylet 46 and the cannula 48 are inserted into the patient near the biopsy area. The stylet 46 is then released into the biopsy area (FIG. 28d) by advancing the stylet extension 82 by pushing on the second pushing portion 99 or the back of pushing portion 88 with user's thumb so that the tissue is pierced and relaxes into the notch 50 of the stylet (shown in FIG. 26b). Once the stylet extension 82 is pushed forward by the user's thumb and the stylet advances, the cannula is then automatically actuated as explained hereinafter. The trip protrusion 120 which is connected to stylet 82 deflects the stylet locking member protrusion 119 thereby releasing the first locking member 118 from the second locking member 117 on the stylet coupling. Thereafter, the actuating pin 116 located on the stylet coupling hits the front projection 125 of actuating arm 110 and then the back projection 110a of the actuating arm deflects the cannula locking member protrusion 124. The cannula is released (the first locking member 122 of the cannula disengages the second locking member 123) and then rapidly moves forward so that the tissue in the notch is severed and retained in the notch of the stylet (FIG. 26d). The stylet and cannula are together disengaged from the biopsy site. The stylet 46 and the cannula 48 are both moved rearward by their respective extensions. The cannula 48 is then pressed rearward using the cannula extension 56 so that the tissue sample is exposed and may be removed (FIG. 28b). Moving the stylet extension 82 rearward reestablishes the stylet 46 and the cannula 48 in relation to each other in order to allow subsequent reinsertions into the biopsy area for additional tissue samples.

Figure 31:
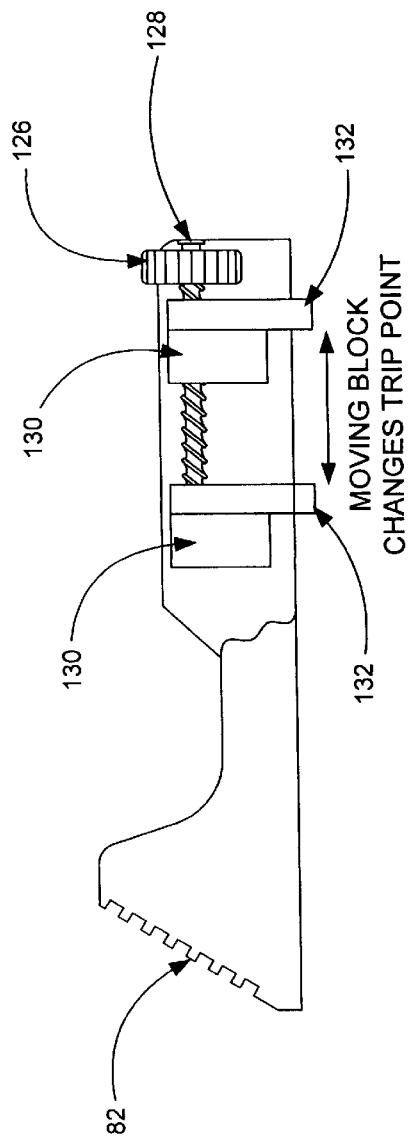
FIG. 31 is a broken away view of an embodiment of the slidable extension of the handle assembly through lines 30—30 of FIG. 30 according to the present invention.

In another embodiment shown in FIGS. 27–30, the handle assembly 40 for the needle set 42 allows the user to obtain a tissue sample from a tissue mass of a predetermined size via an adjustable wheel 126 located on the rear end of the stylet extension 82. Details relating to the handle assembly including the adjustable wheel on the extension are described in Applicants' U.S. patent application Ser. No. 09/076,181 entitled "BIOPSY NEEDLE HANDLE", previously incorporated herein by reference. Similar to the embodiment described heretofore, the cannula extension 56 is urged rearward first. Then stylet extension 82 is urged rearward on the housing 52. Thereafter, the adjustable wheel 126 is turned to the desired depth. The adjustable wheel 126 allows the user to choose the parameters of the needle set 42 to be used to obtain optimal tissue sample for any given biopsy procedure. The adjustable wheel 126 is attached to the stylet extension 82 by a screw member 128. Located on the screw member 128 is a trip bar 130 (FIG. 31). When the adjustable wheel 126 is turned, the desired preset penetration depth of needle is obtained. The trip bar 130 includes a protrusion or tip 132 and moves forward along with the stylet extension 82. The wheel 126 sets the position of the protrusion or tip 132 relative to the stylet extension 82. The stylet extension, together with the trip bar 132 are pushed forward, thus urging the stylet 46 forward the preset length, until the trip bar protrusion or tip 132 interacts with the first locking member protrusion 119 (FIG. 15) as explained heretofore. Also provided on the top of the stylet extension is a window 134 which displays a corresponding numeric indicator of the desired set penetration depth. The penetration depth may be set from 13 mm to 21 mm (FIGS. 27–29) and is the distance that the needle set is urged forward into the biopsy area. It is understood that smaller and larger lengths can be possible with the same basic design as is understood by one skilled in the art.

Accordingly, the present invention provides for an inventive handle assembly and needle set which simplifies the biopsy procedure and which is easy to use and make. The handle assembly allows for manual manipulation to the utmost simplicity by incorporating the cocking of the cannula and stylet, the safety feature and the firing mechanism in a single assembly, thus allowing real single-handed operation without the need of separate components, buttons or slides to activate each of these actions. The disposable handle assembly thus affords an uncomplicated design allowing the handle to be inexpensive to fabricate and more compact.

It is understood that the handle assembly and a needle set having a particular needle length (for obtaining a tissue sample of a predetermined size) may be preassembled when manufactured and made available to a physician as a packaged and sterilized device. This would be advantageous to the physician who routinely uses one particular sized needle set in a biopsy procedure.

Although the invention has been described in detail herein, it should be understood that the invention is not limited to the embodiment herein disclosed. Various changes, substitutions and modifications may be made thereto by those skilled in the art without departing from the spirit or scope of the invention as described and defined by the appended claims.

INDUSTRIAL APPLICABILITY

The advantages of the present invention include a handle assembly for a needle set which single-handedly and automatically captures a tissue sample from a tissue mass. The handle assembly incorporates the cocking of the cannula and stylet, the safety feature and the firing mechanism in a single assembly without the need of separate components, buttons or slides to activate each of these actions.

Other features, aspects and objects of the invention can be obtained from a review of the figures and the claims.

It is to be understood that other embodiments of the invention can be developed and fall within the spirit and scope of the invention and claims.

I claim:

1. A biopsy handle capable of receiving a needle set assembly having a stylet adapted for piercing and storing a tissue sample and a cannula adapted for severing and trapping the tissue sample, the biopsy handle comprising:
   a housing adapted for accepting the needle set;
   a first actuator slidably attached to the housing and adapted for selectively positioning the cannula relative to the housing;
   a second actuator slidably attached to the housing and adapted for selectively positioning the stylet relative to the housing; and
   said first actuator and said second actuator both including an element which is adapted to allow said first actuator and said second actuator to be slid in a forward and a reverse direction with respect to the housing in order to move the cannula and the stylet relative to the housing using a single digit of a single hand of a user.

2. The biopsy handle of claim 1 wherein:
   said first actuator and said second actuator each have a slidable base that is slidably attached to said housing; and
   said element of said first actuator and said element of said second actuator include a projection from said slidable base, which projection has first and second sides, which first and second sides are adapted to be urged by the single hand of the user, with urging on the first side for moving said second actuator forwardly and urging on the second side for moving said first actuator and said second actuator rearwardly.

3. The biopsy handle of claim 1 further including:
   a locking lid located on a bottom of said housing which can be moved from an open position in order to accept the needle set into said housing to a closed and locked position in order to lockingly contain the needle set in the housing.

4. The biopsy handle of claim 3 wherein:
   said locking lid is adapted for allowing single use of the housing.

5. The biopsy handle of claim 3 wherein:
   one of said lid and said housing includes at least one catch and the other of said lid and said housing includes at least one receptacle which receives said catch for locking the needle set in the housing.

6. The biopsy handle of claim 5 wherein:
   said catch is wedge shaped with a ramp and a back edge, and
   wherein said ramp allows said catch to be urged in to said receptacle and said back edge locks said catch in said receptacle.

7. The biopsy handle of claim 1 wherein the element is a protrusion adapted to be engaged by a single digit of a single hand of a user.

8. A method of taking a tissue biopsy with a biopsy handle which includes a housing that has a movable actuator and which handle is adapted for receiving a needle set including a stylet and a cannula, the steps including:
   loading the needle set into the handle;
   using a single hand in order to hold the handle and a single digit of said single hand to move a first actuator in order to lock the cannula against an urging force;
   using a single hand in order to hold the handle and a single digit of said single hand to move a second actuator in order to lock the stylet against an urging force, and
   using the same single hand in order to continue to hold the handle and a single digit of said single hand to move the second actuator in order to advance the stylet into tissue to be biopsied and automatically advance the cannula over the stylet in order to capture tissue.

9. The method of claim 8, including the further step of:
   using a single digit of the same single hand in order to move the actuator in order to move the cannula relative to the stylet in order to have access to any tissue captured between the stylet and the cannula.

10. A biopsy handle capable of receiving a needle set assembly having a stylet adapted for piercing and storing a tissue sample and a cannula adapted for severing and trapping the tissue sample, the biopsy handle comprising:
    a housing adapted for accepting the needle set;
    a first extension slidably attached to said housing adapted for urging the cannula rearward;

a second extension slidably attached to said housing adapted for urging the stylet rearward;

said second extension having an activating means for urging the stylet forward into a tissue sample and automatically actuating the cannula; and wherein said first extension and said second extension are located side by side and are slidable along parallel lines.

11. The handle of claim 10, wherein:

said handle is adapted for one hand operation.

12. The handle of claim 10, wherein:

said first extension and said second extension have a portion extending therefrom which adapts the handle for one-hand operation.

13. The biopsy handle as recited in claim 10, wherein said housing includes a cannula coupling that couples said first extension to the cannula and a stylet coupling that couples said second extension to the stylet.

14. A biopsy handle adapted for accepting a needle set having a stylet and a cannula, the handle comprising:

a housing;

a first guide secured to said housing;

a second guide secured to said housing;

a first actuator slidably mounted on said housing;

a second actuator slidably mounted on said housing;

wherein said first actuator and said second actuator are located side by side and are slidable along parallel lines;

a first pin associated with said first guide;

a second pin associated with said second guide;

said first pin adapted to engage a cannula of a needle set;

said second pin adapted to engage a stylet of a needle set;

a first spring associated with said first guide and said first pin;

a second spring associated with said second guide and said second pin;

a first pushing member that is associated with said first pin in order to urge said first pin relative to said first guide and against said first spring;

a second pushing member that is associated with said second pin in order to urge said second pin relative to said second guide and against said second spring; and said first pin and said first pushing member operatively associated with said first actuator such that as said first actuator slides relative to said housing, said first pin and said first pushing member move relative to said housing and along said first guide in order to urge the cannula into a first operable position.

15. The handle of claim 14, further including:

said second pin and said second pushing member operatively associated with said second actuator such that as said second actuator slides relative to said housing, said second pin and said second pushing member move relative to said housing and along said second guide in order to urge the stylet into a second operable position.

16. The handle of claim 15, further including:

said housing having a third locking member;

said second pin having a fourth locking member;

and with the stylet in the second operable position such that said second pin is urged against said second spring, said third locking member engages said fourth locking member in order to lock said second pin in the second operable position relative to said housing.

17. The handle of claim 16 further including:

a trip pin;

said trip pin associated and movable with said second actuator;

said trip pin being capable of contacting said third locking member in order to release said fourth locking member and thereby allow said second spring to move said second pin and thus the stylet relative to said housing.

18. The handle of claim 14, further including:

said housing having a first locking member;

said first pin having a second locking member;

and with the cannula in the first operable position such that said first pin is urged against said first spring, said first locking member engages said second locking member in order to lock said first pin in the first operable position relative to said housing.

19. The handle of claim 18, further including:

an actuating pin;

said actuating pin associated and movable with said second actuator;

said actuating pin being capable of contacting an actuating arm, said actuating arm also being capable of contacting said first locking member in order to release said second locking member and thereby allow said first spring to move said first pin and thus the cannula relative to said housing.

20. A biopsy handle adapted for accepting a needle set having a stylet with a stylet base with a first aperture, and a cannula with a cannula base with a second aperture, with the stylet and cannula movable relative to each other as the stylet base and the cannula base move relative to each other, said biopsy handle comprising:

a housing;

a first guide rod secured to said housing and adapted to receive the stylet base adjacent thereto such that said stylet base can move along said first guide rod;

a second guide rod secured to said housing and adapted to receive the cannula base adjacent thereto such that said cannula base can move along said second guide rod;

said first guide rod and said second guide rod being substantially parallel to each other;

a first actuator slidably mounted on said housing;

a second actuator slidably mounted on said housing;

a first pin that is movable along said first guide rod;

a second pin that is movable along said second guide rod;

said first pin adapted to engage the first aperture of the stylet base of the needle set;

said second pin adapted to engage the second aperture of the cannula base of the needle set;

a first spring associated with said first guide rod and said first pin;

a second spring associated with said second guide rod and said second pin;

a first pushing member that is associated with said first pin in order to urge said first pin relative to said first guide and against said first spring;

a second pushing member that is associated with said second pin in order to urge said second pin relative to said second guide and against said second spring; and said first pin and said first pushing member operatively associated with said first actuator such that as said first actuator slides relative to said housing, said first pin and said first pushing member move relative to said housing and along said first guide in order to urge the cannula into a first operable position.

21. The handle of claim 20, further including:

said second pin and said second pushing member operatively associated with said second actuator such that as said second actuator slides relative to said housing, said second pin and said second pushing member move relative to said housing and along said second guide in order to urge the stylet into a second operable position.

22. The handle of claim 21, further including:

said housing having a third locking member;

said second pin having a fourth locking member;

and with the stylet in the second operable position such that said second pin is urged against said second spring, said third locking member engages said fourth locking member in order to lock said second pin in the second operable position relative to said housing.

23. The handle of claim 22 further including:

a trip pin;

said trip pin associated and movable with said second actuator;

said trip pin being capable of contacting said third locking member in order to release said fourth locking member and thereby allow said second spring to move said second pin and thus the stylet relative to said housing.

24. The handle of claim 20, further including:

said housing having a first locking member;

said first pin having a second locking member;

and with the cannula in the first operable position such that said first pin is urged against said first spring, said first locking member engages said second locking member in order to lock said first pin in the first operable position relative to said housing.

25. The handle of claim 24, further including:

an actuating pin;

said actuating pin associated and movable with said second actuator;

said actuating pin being capable of contacting an actuating arm, said actuating arm also being capable of contacting said first locking member in order to release said second locking member and thereby allow said first spring to move said first pin and thus the cannula relative to said housing.

26. A biopsy handle adapted for accepting a needle set having a stylet and a cannula, the biopsy handle comprising:

a housing;

a first actuator slidably mounted to said housing;

a second actuator slidably mounted to said housing and adjacent to said first actuator;

wherein said first and second actuators are located side by side and are slidable along parallel lines;

said housing including a cavity adapted for receiving the needle set;

said first actuator including a first member adapted for operably engaging the cannula;

said second actuator including a second member adapted for operably engaging the stylet;

said housing including an actuating member adapted for causing the cannula to be urged over the stylet after the stylet has been inserted.

27. The biopsy handle of claim 26, wherein said first actuator and said second actuator includes a first extension and a second extension, respectively.

28. The biopsy handle of claim 26, further including:

said housing having a first locking member;

a second locking member which is operably associated with the first member and adapted to be operably associated with the cannula such that said first member can urge said second locking member in order to urge said cannula into a position;

said housing having a third locking member;

a fourth locking member which is operably associated with the second member and adapted to be operably associated with the stylet such that said second member can urge said fourth locking member in order to urge said stylet into a position; and said second locking member capable of lockingly engaging said first locking member in order to lock the cannula into a position and said third locking member capable of lockingly engaging said fourth locking member in order to lock the stylet into a position.

29. The biopsy handle of claim 25 wherein said first actuator and said second actuator each include a protrusion that is adapted to be engaged by a single digit of a single hand of a user.

30. The biopsy handle of claim 25 wherein the actuating member automatically causes the cannula to be urged over the stylet.

31. A biopsy handle adapted for accepting a needle set having a stylet and a cannula, the handle comprising:

a housing;

a first guide secured to said housing;

a second guide secured to said housing;

a first actuator slidably mounted on said housing;

a second actuator slidably mounted on said housing;

a first pin associated with said first guide;

a second pin associated with said second guide;

said first pin adapted to engage a cannula of a needle set;

said second pin adapted to engage a stylet of a needle set;

a first spring associated with said first guide and said first pin;

a second spring associated with said second guide and said second pin;

a first pushing member that is associated with said first pin in order to urge said first pin relative to said first guide and against said first spring;

a second pushing member that is associated with said second pin in order to urge said second pin relative to said second guide and against said second spring; and said first pin and said first pushing member operatively associated with said first actuator such that as said first actuator slides relative to said housing, said first pin and said first pushing member move relative to said housing and along said first guide in order to urge the cannula into a first operable position;

said housing having a first locking member;

said first pin having a second locking member; and and with the cannula in the first operable position such that said first pin is urged against said first spring, said first locking member engages said second locking member in order to lock said first pin in the first operable position relative to said housing.

32. A biopsy handle adapted for accepting a needle set having a stylet and a cannula, the handle comprising:

a housing;

a first guide secured to said housing;

a second guide secured to said housing;
a first actuator slidably mounted on said housing;
a second actuator slidably mounted on said housing;
a first pin associated with said first guide;
a second pin associated with said second guide;
said first pin adapted to engage a cannula of a needle set;
said second pin adapted to engage a stylet of a needle set;
a first spring associated with said first guide and said first pin;
a second spring associated with said second guide and said second pin;
a first pushing member that is associated with said first pin in order to urge said first pin relative to said first guide and against said first spring;
a second pushing member that is associated with said second pin in order to urge said second pin relative to said second guide and against said second spring; and
said first pin and said first pushing member operatively associated with said first actuator such that as said first actuator slides relative to said housing, said first pin and said first pushing member move relative to said housing and along said first guide in order to urge the cannula into a first operable position;
said second pin and said second pushing member operatively associated with said second actuator such that as said second actuator slides relative to said housing, said second pin and said second pushing member move relative to said housing and along said second guide in order to urge the stylet into a second operable position;
said housing having a first locking member;
said second pin having a second locking member; and
and with the stylet in the second operable position such that said second pin is urged against said second spring, said first locking member engages said second locking member in order to lock said second pin in the second operable position relative to said housing.

33. The handle of claim 32 further including:
a trip pin;
said trip pin associated and movable with said second actuator;
said trip pin being capable of contacting said first locking member in order to release said second locking member and thereby allow said second spring to move said second pin and thus the stylet relative to said housing.

34. The handle of claim 32 further including:
said housing having a third locking member;
said first pin having a fourth locking member;
and with the cannula in the first operable position such that said first pin is urged against said first spring, said third locking member engages said fourth locking member in order to lock said first pin in the first operable position relative to said housing;
an actuating pin;
said actuating pin associated and movable with said second actuator;
said actuating pin being capable of contacting an actuating arm, said actuating arm also being capable of contacting said third locking member in order to release said fourth locking member and thereby allow said first spring to move said first pin and thus the cannula relative to said housing.

35. A biopsy handle adapted for accepting a needle set having a stylet and a cannula, the biopsy handle comprising:
a housing;
a first actuator slidably mounted to said housing;
a second actuator slidably mounted to said housing and adjacent to said first actuator;
said housing including a cavity adapted for receiving the needle set;
said first actuator including a first member adapted for operably engaging the cannula;
said second actuator including a second member adapted for operably engaging the stylet;
said housing including an actuating member adapted for causing the cannula to be urged over the stylet after the stylet has been inserted;
said housing having a first locking member;
a second locking member which is operably associated with the first member and adapted to be operably associated with the cannula such that said first member can urge said second locking member in order to urge said cannula into a position;
said housing having a third locking member;
a fourth locking member which is operably associated with the second member and adapted to be operably associated with the stylet such that said second member can urge said fourth locking member in order to urge said stylet into a position; and
said second locking member capable of lockingly engaging said first locking member in order to lock the cannula into a position and said third locking member capable of lockingly engaging said fourth locking member in order to lock the stylet into a position.

* * * * *